United States Patent [19]

Gargan

[11] Patent Number: 5,487,892
[45] Date of Patent: Jan. 30, 1996

[54] METHOD FOR TREATING THROMBOTIC DISEASE USING A FIBRIN SPECIFIC MONOCLONAL ANTIBODY

[75] Inventor: Paul E. Gargan, South Bend, Ind.

[73] Assignee: American Biogenetic Sciences, Inc., Copiague, N.Y.

[21] Appl. No.: 204,015

[22] Filed: Feb. 24, 1994

[51] Int. Cl.$^6$ .......................... A61K 39/395; C07K 16/18
[52] U.S. Cl. .................................... 424/145.1; 424/158.1; 530/388.25; 530/388.1
[58] Field of Search ............................. 424/145.1, 158.1; 530/388.25, 388.1

[56] References Cited

U.S. PATENT DOCUMENTS

| | | |
|---|---|---|
| 4,722,903 | 2/1988 | Kudryk et al. |
| 4,758,524 | 7/1988 | Bundesen et al. |
| 4,916,070 | 4/1990 | Matsueda et al. |
| 5,091,512 | 2/1992 | Gargan et al. |
| 5,120,834 | 6/1992 | Gargan et al. |
| 5,223,410 | 6/1993 | Gargan et al. |

FOREIGN PATENT DOCUMENTS 0478366  9/1991  European Pat. Off.

OTHER PUBLICATIONS

Waldmann, T. A., Science, 252:1657–1662, Jun. 21, 1991.
Harris, W. J. et al., TibTech, 11:42–44, Feb. 1993.
Hui, K. Y. et al., Fibrinolysis, 4 (Supp. 3): 25, 1990.
Gargan, P. E. et al., Fed. Am. Soc. Exp. Biol, J5 (4): A464, 1991 (Apr. 21–25).
Rosebrough, S. F. et al., J. Nucl. Med., 31(6):1048–1054, 1990.
Bang and Chang, 1974, "Soluble fibrin complexes", in: Semin Thromb Hemost 1(2):91–128.
Cierniewski and Budzynski, 1992, "Involvement of the αchain in fibrin clot formation. Effect of monoclonal antibodies", Biochemistry 31(17):4248–4253.
Francis et al., 1985, "Some studies with a monoclonal antibody directed against human fibrinogen", Am J Hematol 18:111–119.
Gargan et al., 1993, "A monoclonal antibody which recognizes an epitopic region unique to the intact fibrin polymeric structure", Fibrinolysis 7(4):275–283.
Gargan et al., 1988, "A fibrin specific monoclonal antibody which interferes with the fibrinolytic effect of tissue plasminogen activator", Thrombosis and Haemostasis 59(3):426–431.
Gimple et al., 1992, "Effect of chronic subcutaneous or intramural administration of heparin on femoral artery restenosis after balloon angioplasty in hypercholesterolemic rabbits", Circulation 86(5):1536–1546.
Hoots et al., 1981, "A naturally occurring antibody that inhibits fibrin polymerization", New Engl J Med 304(15):857–861.
Ip et al., 1991, "The role of platelets, thrombin, and hyperplasia in restenosis after coronary angioplasty", J Am Coll Cardiol 17(6):77B–88B.
Knight et al., 1988, "Evaluation of Indium–111–labeled anti–fibrin antibody for imaging vascular thrombi", J Nucl Med 29:494–502.
Kudryk et al., 1991, "Fibrinogen–fibrin: Preparation and use of monoclonal antibodies as diagnostics", Biotechnology 19:281–313.
Liau et al., 1987, "Evaluation of monoclonal antifibrin antibodies by their binding to human blood clots", Thrombosis and Haemostatis 57(1):49–54.
Lill et al., 1993, "A new immunoassay for soluble fibrin enables a more sensitive detection of the activation state of blood coagulation in vivo", Blood Coagulation and Fibrinolysis 4:97–102.
Marciniak and Greenwood, 1979, "Acquired coagulation inhibitor delaying fibrinopeptide release", Blood 53(1):81–92.
Matsueda and Margolies, 1986, "Structural basis for the species selectivity of a fibrin–specific monoclonal antibody", Biochemistry 25:1451–1455.
Mirshahi et al., 1990, "A monoclonal antibody to fibrinogen inhibiting fibrin polymerization", Fibrinogen 4. Current Basic And Clinical Aspects: Proceedings of the Intl Fibrinogen Workshop, Kyoto, Japan, pp. 49–54.
Müller–Berghaus et al., 1985, "Detection of fibrin in plasma by a monoclonal antibody against the amino–terminus of the alpha–chain of fibrin", Scand J Clin Lab Invest 45(Suppl 178):145–151.
Nieuwenhuizen, 1993, "Soluble fibrin as a molecular marker for a pre–thrombotic state: A mini–review", Blood Coagulation and Fibrinolysis 4:93–96.
Nieuwenhuizen et al., 1992, "A rapid monoclonal antibody–based enzyme immunoassay (EIA) for the quantitative determination of soluble fibrin in plasma", Thrombosis and Haemostasis 68(3):273–277.
Scheefers–Borchel et al., 1985, "Discrimination between fibrin and fibrinogen by a monoclonal antibody against a synthetic peptide", Proc Natl Acad Sci USA 82:7091–7095.
Selmayr et al., 1985, "Crosslinking of soluble fibrin and fibrinogen", Thrombosis Research 39:467–474.
Selmayr and Müller–Berghaus, 1985, "Soluble–crosslinked fibrin(ogen) polymers", Thrombosis and Haemostasis 54(4):804–807.
Sobel et al., 1988, "Early alpha chain crosslinking in human fibrin preparations", Thrombosis and Haemostasis 60(2):153–159.
Sola et al., 1983, "Isolation and characterization of a monoclonal antibody specific for fibrinogen and fibrin of human origin", Thrombosis Research 29:643–653.
Tymkewycz et al., 1993, "Generation and partial characterization of five monoclonal antibodies with high affinities for fibrin", Blood Coagulation and Fibrinolysis 4:211–221.
Wasser et al., 1990, "Thrombus detection using Tc–99m labeled antifibrin monoclonal antibody (MoAb) experiments in vitro and in animals", Thrombosis Research Supplement X:91–104.

Primary Examiner—Margaret Parr
Assistant Examiner—Susan A. Loring
Attorney, Agent, or Firm—Pennie & Edmonds

[57] ABSTRACT

Methods for the use of a fibrin-specific antibody for in vivo inhibition of thrombus formation. Pharmaceutical compositions, as well as kits, for use in such methods are also provided.

26 Claims, 2 Drawing Sheets

METHOD FOR TREATING THROMBOTIC DISEASE USING A FIBRIN SPECIFIC MONOCLONAL ANTIBODY

FIELD OF THE INVENTION

The subject invention relates methods for the use of a fibrin-specific antibody for in vivo inhibition of thrombus formation. Pharmaceutical compositions for use in such methods are also provided.

BACKGROUND OF THE INVENTION

Thrombus Formation from Disease or Surgery

Blood clots, or thrombi, form at the sites of blood vessel injury. The clinical manifestations of pathological thrombosis or thrombotic disease are extremely diverse and include deep vein thrombosis (DVT), and arterial and venous thrombosis. Thromboembolism and thrombotic complications of other vascular disease (e.g., atherosclerosis) can result in occlusion of major arteries leading to organ ischemia and the attendant life-threatening conditions such as cerebrovascular accident (stroke), myocardial infarction, etc.

In addition, invasive surgical procedures, including but not limited to balloon angioplasty, and organ transplantation (both natural and artificial), can trigger thrombus formation. For example, balloon angioplasty, a procedure used to clear occluded arteries, can actually injure the arterial vessel wall, triggering reocclusion by new thrombus deposition. One report states that percutaneous transluminal coronary angioplasty remains plagued by a 25–35% frequency of reocclusion of the vessel. Gimple, L. W., et al., *Circulation*, 86:1536–46 (1992). See also Sarembock, I. J., et al., *Circulation*, 80:1029–40 (1989); and Ip, J. H., et al., *JACC*, 17:77B–88B (1991). In fact, one report states that "the mechanism of angioplasty, involving in most cases endothelial damage and plaque fracture or dissection [ref.], is very similar to the process that leads to the acute ischemic syndromes." Tenaglia, A. N., *Ann. Rev. Med.*, 44:465–79, 466 (1993).

Since systemic treatment with anticoagulants such as heparin and coumarin have been shown to have little or no effect in preventing post-angioplasty reocclusion (Ip, J. H., et al., *JACC*, 17:77B–88B (1991)), and since such anticoagulant treatments often risk systemic hemorrhage in patients (*Physicians' Desk Reference*, 47th Ed., Medical Economics Data (1993)), new site-specific methods of treatment to inhibit or interfere with thrombus formation, both in the case of pre-existing vascular disease and for invasive surgical procedures, would be useful.

The Hemostatic System

The hemostatic mechanism whereby a thrombus is formed is a complex physiological response mechanism involved in repairing damage to an injured blood vessel. See Harker, L. A., and Mann, K. G., "Thrombosis and Fibrinolysis" in: *Thrombosis in Cardiovascular Disorders*, Fuster, V. and Verstraete, M. (eds), W. B. Saunders Co. (1992), pp. 1–16.

Hemostasis is achieved through cooperative interactions among the wall of the damaged blood vessel, the platelets and the coagulation system. See Furie, B. and Furie, B. C., *Cell*, 53:505–18 (1988).

The role of the coagulation system is to provide an insoluble fibrin matrix to stabilize and anchor a platelet plug which has been assembled on the subendothelial structure of the damaged vessel at the site of the injury. Coagulation is an amplification process involving a chain of enzymatic reactions in which proenzymes (clotting factors) are activated sequentially to form active enzymes. The formation of the fibrin matrix from circulating fibrinogen is the result of this cascading sequence of enzymatic reactions resulting in the explosive production of the enzyme thrombin at the required site, the conversion by thrombin of fibrinogen to fibrin, and the crosslinking of fibrin by Factor XIIIa, thereby forming the thrombus.

The sequence of reactions can be simply represented by a three step process as follows:

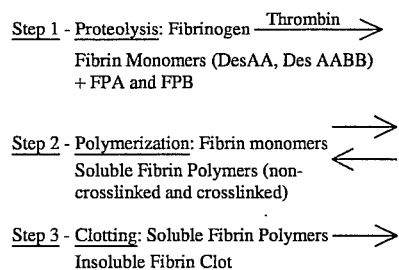

Fibrinogen is composed of three pairs of non-identical polypeptide chains: $A\alpha$, $B\beta$ and $\gamma$. See L. Stryer, *Biochemistry*, 3rd Ed., W. H. Freeman and Company New York (1988), p. 249. In the initial step, whereby fibrinogen is converted to fibrin, shown above in step 1, fibrinogen is cleaved by thrombin to release fibrinopeptide A (FPA) from the amino-terminal ends of the two fibrinogen $A\alpha$-chains. The remaining portion of the fibrinogen molecule is a "fibrin monomer" designated DesAA. As also shown in step 1, thrombin simultaneously (but more slowly) also cleaves fibrinopeptide B (FPB) from the amino-terminal ends of the two fibrinogen $B\beta$-chains. The remaining portion of the fibrinogen molecule after this second cleavage event is also a fibrin monomer, designated DesAABB. As a result of the release of FPA and FPB, new amino-terminal ends are exposed on the $\alpha$ and $\beta$ chains of the fibrin monomer. See W. Nieuwenhuizen, *Blood Coagulation and Fibrinolysis* 4:93–96 (1993). In step 2, the fibrin monomers spontaneously begin to form inter-monomer non-covalent bonds (non-crosslinked) to form a soluble polymer. Factor XIIIa acts on this polymer by enzymatically adding covalent crosslinks between the fibrin monomer units. A crosslinked polymer can remain soluble, but at some point during the processes of polymerization and crosslinking, the fibrin polymer becomes insoluble, forming a fibrin clot, as indicated in step 3.

Soluble fibrin polymers are the immediate precursors of the fibrin clot. Consequently, plasma levels of soluble fibrin polymers are believed to be elevated in individuals with impending or existing thrombosis. The detection and measurement of the amount of these polymers in blood, in particular the DesAABB soluble fibrin polymers, have been shown to be useful as an indication of incipient blood clot formation. See Nieuwenhuizen, p. 94; and Marder et al., U.S. Pat. No. 5,206,140.

Antibodies Directed to Components of the Hemostatic System

Both naturally-occurring and laboratory-raised antibodies have played a role in characterizing the components of the hemostatic system and in elucidating their functions.

Marciniak, E., and Greenwood, M. F., *Blood*, 53; 81–92 (1979), describe the case of an inhibitor of blood clotting in the serum of a 14-year old patient with Down syndrome, which was present in the IgG fraction and which inhibited the enzymatic release of fibrinopeptide A from fibrinogen. Hoots, W. K., et al., *New Eng. J. Med.*, 304:857–61 (1981), describe the case of a 13-year old patient suffering from chronic aggressive hepatitis as well as a coagulation defect, in which the defect was traced to the presence of antibodies in the patient's blood that expressed high affinity to both fibrinogen and fibrin, and which inhibited the polymerization of fibrin monomers, thus preventing the formation of a fibrin gel.

Sola, B., et al., *Thromb. Res.*, 29:643–53 (1983), describe the establishment of a hybridoma cell line secreting monoclonal antibodies specific for both human fibrinogen and fibrin. Elms, M. J., et al., *Thromb. Haemostas*, 50:591–94 (1983), describe preparation of a hybridoma cell line secreting monoclonal antibodies which recognize an antigenic determinant in the D dimer, a specific fragment resulting from the degradation of cross-linked fibrin. Hui, K. Y., et al., *Science*, 222:1129–32 (1983), and Scheefers-Borchel, U., et al., *Proc. Natl. Acad. Sci. USA*, 82:7091–95 (1985), describe the use as antigens of synthetic hexapeptides representing the amino terminus of the α or β chain, respectively, of human fibrin to produce monoclonal antibodies that bind to fibrin even in the presence of fibrinogen. Kudryk, B., et al., *Mol. Immunol.*, 21:89–94 (1984), describe the preparation of a hybridoma cell line secreting monoclonal antibodies directed to the N-DSK portion of fibrinogen. Sobel, J. H., et al., *Thromb. and Haem.*, 60:153–59 (1988), describe the use of two different monoclonal antibodies that bind to CNBr Aα chain fragments of fibrinogen to investigate early α chain cross-linking events between neighboring fibrin molecules. Mirshahi, M., et al., *Fibrinogen*, 4:49–54 (1990), describe preparation of a hybridoma cell line that secretes monoclonal antibodies directed to fibrinogen which are able to inhibit fibrin polymerization. Cierniewski, C. S., and Budzynski, A. Z., *Biochemistry*, 31:4248–53 (1992), describe the preparation and use of polyclonal and monoclonal antibodies directed against purified human fibrinogen that inhibit the polymerization rate of fibrin monomers and well as interfere with the action of thrombin on fibrinogen. Tymkewycz, P.M., et al., *Blood Coag. and Fibrinol.*, 4:211–21 (1993), describe the production of five monoclonal antibodies with high affinity for fibrin, and which do not react with fibrinogen. Gargan, P. E., et al., *Fibrinolysis*, 7:275–83 (1993), describe the establishment of a hybridoma cell line, MH-1, which produces monoclonal antibodies specific to both the crosslinked and noncrosslinked fibrin polymeric structure, but with no detectable immunoreactivity to fibrinogen nor to any degradation products of fibrin or fibrinogen. In addition, the MH-1 antibody does not react with DesAA or DesAABB fibrin monomer, nor was any reactivity with the individual α, β, or γ chains of fibrinogen detected.

For further discussion on the use of monoclonal antibodies specific to components of the hemostatic system, see Kudryk, B. J., et al., "Monoclonal Antibodies as Probes for Fibrin(ogen) Proteolysis" in: *Monoclonal Antibodies in Immunoscintigraphy*, Chatal, J-F (ed), CRC Press, Boca Raton, Fla. (1989), pp. 365–398.

Modified antibodies directed to hemostatic components have been developed for clinical use as agents for thrombus imaging in situ. See, for example, Liau, C-S, and Su, C-T, *J. Form. Med. Assoc.*, 88:209–12 (1989); Wasser, M. N. J. M., et al., *Blood*, 74:708–14 (1989); Walker, K. Z., et al., *Eur. J. Nucl. Med.*, 16:787–94 (1990); Alavi, A., et al., *Radiology*, 175:79–85 (1990); Wasser, M. N. J. M., et al., *Thromb. Res.*, Supp. X: 91–104 (1990); and Kanke, M., et al., *J. Nucl. Med.*, 32:1254–60 (1991).

Antibodies to fibrin, conjugated to thrombolytic enzymes, have been developed for therapeutic use. See, for example, Bode, C., et al., *Science*, 229:765–67 (1985). In this report, the site-specific delivery of thrombolytic agent appears to have significantly increased the agent's efficacy at lysing clots.

Finally, several U.S. patents have issued that are directed toward preparation and/or methods of use of monoclonal antibodies specific to fibrinogen, fibrin, or to degradation products thereof. See U.S. Pat. Nos. 4,722,903; 4,758,524; and 4,916,070, which listing is not intended to be exhaustive.

Methods to Prevent Thrombus Formation

Antithrombotic therapy typically includes administration of one or more anticoagulants, such as heparin or coumarin. *Physicians' Desk Reference*, 47th Ed., Medical Economics Data (1993); *The Merck Manual of Diagnostics and Therapy*, 15th Ed., Merck Sharpe & Dohme Research Labs (1987). These anticoagulants are frequently used in an attempt to prevent recurrent thrombosis in patients suffering from vascular disease, and in an attempt to prevent acute thrombotic reocclusion after angioplasty.

A major disadvantage of using such systemic anticoagulants is that of risking systemic hemorrhage. Administering physicians are warned that "[h]emorrhage can occur at virtually any site in patients receiving heparin." *Physicians' Desk Reference*, 47th Ed., Medical Economics Data (1993), p. 2568.

In addition, the efficacy of such anticoagulants in preventing reocclusion after angioplasty has been shown to either be no different from that of placebo treatments, or irreproducible. (Ip, J. H., et al., *JACC*, 17:77B–88B (1991)). Accordingly, the advantage in using such anticoagulants is counterbalanced by both the risk of hemorrhage and by their questionable efficacy in preventing reocclusion.

Numerous biological and mechanical strategies have been utilized in an attempt to reduce the rate of reocclusion after angioplasty, but no therapy has shown consistent positive results. Accordingly, there is an increasing interest in "site-specific" or "direct" delivery of anti-thrombotic agents to the sites of vessel injury. Gimple, L. W., et al., *Circulation*, 86:1536–46 (1992).

Site-specific delivery of anti-thrombotic agents utilizing antibodies directed to appropriate components of the hemostatic system would serve to localize such agents to the site of vessel injury. One advantage of this localization is that a lower administered dose would be required. A second advantage of localization would be reduction of the risk of systemic hemorrhage.

In several cases, antibodies directed to specific components of the hemostatic system have themselves been shown to inhibit fibrin polymerization. Francis, S. E., et al., *Am. J. Hem.*, 18:111–19 (1985), describe studies with a monoclonal antibody generated against fibrinogen that had "mild" anticoagulant activity. Mirshahi, M. et al *Fibrinogen*, 4:49–54 (1990), describe the obtention of a hybridoma cell line secreting monoclonal antibodies, in which the antigen was fragment D, a plasmin degradation product of fibrinogen. These monoclonal antibodies reacted strongly with fibrinogen and inhibited fibrin polymerization. Ciernewski, C. S., and Budzynski, A. Z., *Biochemistry*, 31:4248–53 (1992), describe the obtention of three different hybridoma cell lines, in which the antigen was native human fibrinogen, and which secreted monoclonal antibodies that inhibited the rate of fibrin polymerization.

All three reports are of little or no use, however, in the development of a site-specific therapeutic or prophylactic antithrombotic agent. This is so because in all these cases the antibodies are crossreactive either with fibrinogen or fibrinogen degradation products, all of which are ubiquitous throughout the hemostatic system. Any such antibody administered to a patient would be bound up with fibrinogen or fibrinogen degradation products, and would not be available to inhibit fibrin polymerization or thrombus formation at the site of blood vessel injury.

The subject invention permits one to take a completely different approach to inhibiting thrombus formation by utilizing monoclonal antibodies which are fibrin-specific (i.e., with no significant crossreactivity to fibrinogen or to plasmin-derived degradation products from fibrinogen or fibrin). The subject invention provides a method of using said fibrin-specific monoclonal antibodies that surprisingly inhibits thrombus formation at the site of blood vessel injury.

SUMMARY OF THE INVENTION

The subject invention provides a method for inhibiting thrombus formation at the site of blood vessel injury in a human in need of said inhibition by administration of a fibrin-specific monoclonal antibody. The subject invention further provides fragments or derivatives of a fibrin-specific monoclonal antibody, which fragments and derivatives contain the binding domain of the antibody. The subject invention further provides a pharmaceutical composition comprising a fibrin-specific monoclonal antibody, or fragment or derivative thereof, and a pharmaceutically effective carrier that, in sufficient amount, is effective in inhibiting thrombus formation in a human. The subject invention further provides pharmaceutical kits comprising one or more of the ingredients of the pharmaceutical compositions of the invention.

DETAILED DESCRIPTION OF THE INVENTION

Utility of the Subject Invention

Figure 1:
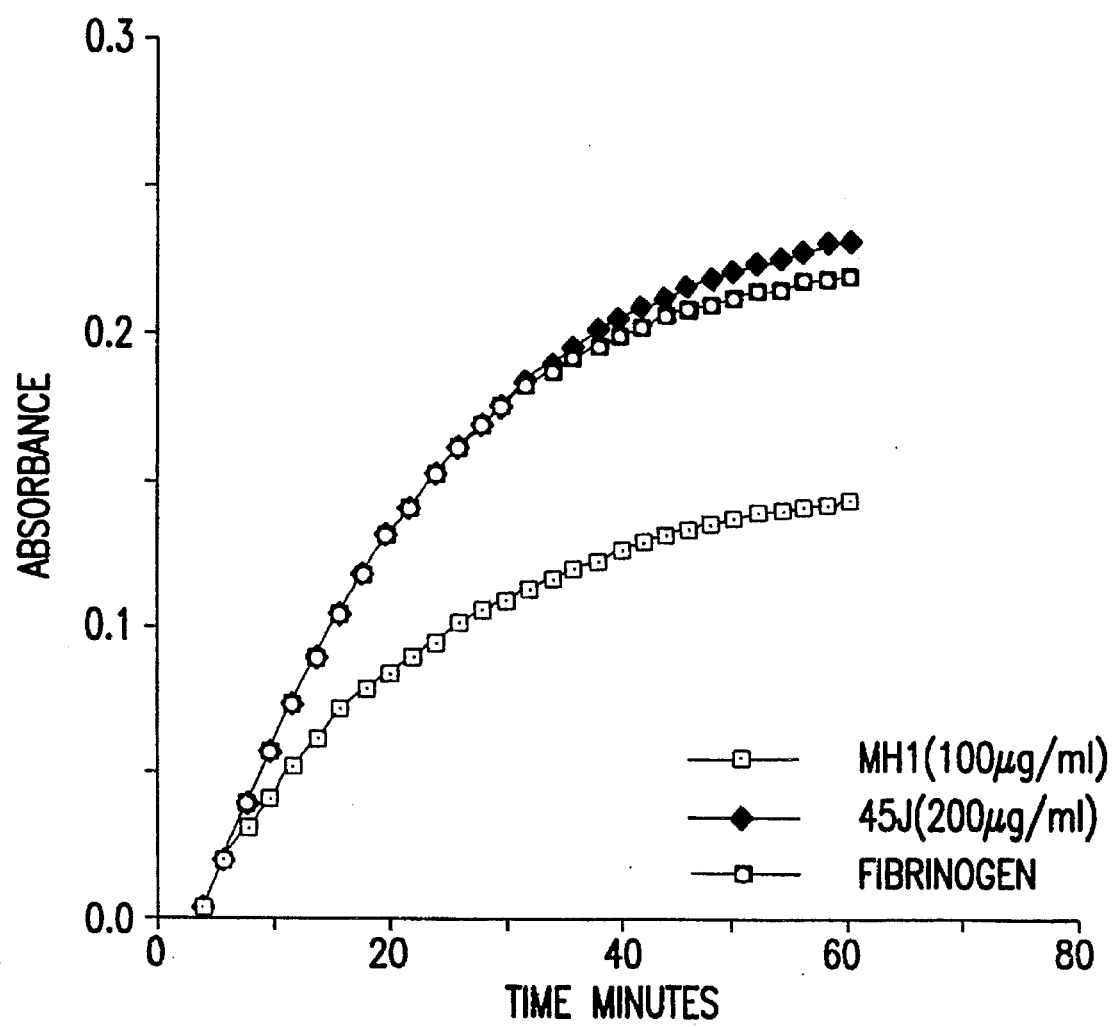
FIG. 1. Inclusion of the MH-1 monoclonal antibody in a fibrinogen/thrombin clotting reaction mixture inhibits both the rate and absolute amount of clotting. "Fibrinogen" and "45J" are control reactions.

It has surprisingly been discovered that a fibrin-specific monoclonal antibody can inhibit fibrin polymerization and thrombus formation. Thus, fibrin-specific monoclonal antibodies can be utilized to prevent or treat any condition in a human that is preventable or treatable by the inhibition of fibrin polymerization or thrombus formation. For example, fibrin-specific monoclonal antibodies are useful in treatment of humans suffering from any vascular disease that involves a risk of pathological thrombosis. Non-limiting examples of such vascular diseases include deep vein thrombosis (DVT), arterial and venous thrombosis, stroke, thromboembolism, pulmonary embolism, and thrombotic complications of atherosclerosis.

Fibrin-specific monoclonal antibodies are also useful, for example, in treatment of humans who are preparing for, undergoing, or recovering from invasive surgical procedures. For purposes of the subject invention, the term "invasive surgical procedure" refers to any surgical procedure that can result in injury to an arterial or venous blood vessel which can lead to thrombotic complications. Non-limiting examples of such procedures include balloon angioplasty, and organ transplantation (both natural and artificial).

In addition to fibrin-specific monoclonal antibodies, antibody fragments which contain the idiotype (binding domain) of the fibrin-specific antibody can be generated by known techniques. For example, such fragments include but are not limited to: (1) F(ab')$_2$ fragments which can be produced by pepsin digestion of the antibody molecule; (2) Fab' fragments which can be generated by reducing the disulfide bridges of the F(ab')$_2$ fragment; and (3) Fab fragments which can be generated by treating the antibody molecule with papain and a reducing agent. Such antibody fragments are included within the scope of the subject invention. For other examples of the preparation and use of antibody fragments, see Parham, P., et al., *J. Immunol. Meth.*, 53:133 (1982); and Khaw, B-A, et al., *J. Nucl. Med.*, 34:2264–68 (1993).

In addition to fibrin-specific monoclonal antibodies and antibody fragments, other antibody derivatives which contain the idiotype (binding domain) of the fibrin-specific antibody can be generated by known techniques. For example, recombinant and synthetic oligopeptides, and analogs thereof, can be synthesized which elicit the same inhibitory effect on thrombus formation as the fibrin-specific monoclonal antibody or fragments thereof. Such derivatives are included within the scope of the subject invention. For other examples of the use of synthetic oligopeptides with sequences based on the primary binding region of a monoclonal antibody, see Knight, L., et al., *J. Nucl. Med.*, 35:282–88 (1994).

Finally, any functionally equivalent fibrin-specific monoclonal antibody, fragment or derivative thereof, is within the scope of the subject invention. By the term "functionally equivalent" is meant any fibrin-specific monoclonal antibody, or fragment or derivative thereof, that is capable in sufficient quantity of inhibiting thrombus formation in a human in need of such treatment by binding to the same epitope to which the MH-1 antibody binds.

Production and Characterization of the MH-1 Monoclonal Antibody

Many of the earlier approaches adopted to raise fibrin-specific antibodies concentrated on immunizing animals with soluble fibrin fragments and synthetic peptides which mimic exposed neoantigenic sites on fibrin. See Hui, K. Y., et al., *Science* 222:1129–32 (1983); Scheefers-Borchel, U., et al., *Proc. Natl. Acad. Sci. USA*, 82:7091–95 (1985); Elms, M. J., et al., *Thromb. Haemostas*, 50:591–94 (1983); and Kudryk, B., et al., *Mol. Immunol.*, 21:89–94 (1984). However, it is believed that the binding site of such antibodies is conserved during the fibrin degradation process and, therefore, such antibodies also may bind to fibrin degradation products.

U.S. Pat. No. 5,120,834 (hereinafter the "'834 patent") by Gargan et al., issued Jun. 9, 1992, which is incorporated herein by reference, generally relates a method to produce monoclonal antibodies from germfree animals by immunizing said germfree animals with an antigen of choice. It is believed that the advantage of using a germfree system with which to produce monoclonal antibodies is that such a system will exhibit a greatly enhanced immune response to the antigen, increasing the likelihood of locating a B-lymphocyte that produces an antibody capable of binding to a specific epitope of the antigen. Such a system has been determined to be particularly useful for generating a highly specific antibody to fibrin, which has little or no crossreactivity to fibrinogen. Raising such a discriminating antibody had been problematic since the structural and conformational similarities between fibrin and fibrinogen is estimated to be greater than 98% (Plow, E. F., et al., *Semin. Thromb. Haemostas*, 8:36 (1982). As a result, only a small percentage of the epitopes on the fibrin molecule are in fact neoantigens (i.e., unique to fibrin).

The '834 patent relates to a hybridoma cell line, ATCC No. HB 9739, secreting monoclonal antibody MH-1. The MH-1 monoclonal antibody is specific to crosslinked and non-crosslinked fibrin polymers, but does not cross-react with fibrinogen or plasmin-derived degradation products of fibrinogen or fibrin.

MH-1 is purified according to the procedures disclosed in the '834 patent. MH-1 binds specifically to fibrin, and does not crossreact with fibrinogen in competition assays. MH-1 does not crossreact with any plasmin-generated fibrinogen degradation products, nor with any plasmin-derived crosslinked fibrin degradation products. As a result, it can be concluded that: (1) MH-1 recognizes an epitope of the intact fibrin molecule which is not present or exposed on the surface of the precursor molecule, fibrinogen; and (2) the epitope is apparently destroyed by plasmin digestion of crosslinked fibrin.

MH-1 was further characterized by Scatchard analysis (Frankel, et al., *Mol. Immunol.*, 16:101–6 (1979)) using $^{125}$I-labelled MH-1 antibody to determine the affinity of MH-1 for fibrin. The value obtained for the dissociation constant $K_D$ was $6.7 \times 10^{-10}$ M, which affinity is about 5,000 times that of tissue plasminogen activator for fibrin.

Western immunoblotting analysis showed that MH-1 does not crossreact with the A$\alpha$, B$\beta$, or $\gamma$ chains of fibrinogen. The same method showed that MH-1 does not crossreact with thrombin-treated A$\alpha$ or B$\beta$ chains of fibrinogen. In addition, ELISA analysis showed that MH-1 reacts with both crosslinked fibrin and non-crosslinked fibrin, with affinity to crosslinked fibrin being the greater of the two.

Methods of Administration

According to the subject invention, fibrin-specific monoclonal antibodies, or fragments or derivatives thereof, are administered to a human in need of treatment to inhibit thrombus formation. The antibodies, or fragments or derivatives thereof, are preferably administered to a human in a form that is unconjugated to any radiolabel, thrombolytic or other agent, or any other molecule or part thereof. However, the methods of the invention can also be carried out using antibodies or derivatives that are conjugated to radiolabels, thrombolytic or other agents, or any molecule or part thereof, and are intended to be encompassed within the scope of the subject invention.

The term "carrier" refers to a diluent, excipient, or vehicle with which the fibrin-specific monoclonal antibody, or fragment or derivative thereof, is administered.

The term "pharmaceutically acceptable carrier" means that the carrier is approved by a regulatory agency of the Federal or a state government or listed in the U.S. Pharmacopeia or other generally recognized pharmacopeia for use in animals, and more particularly in humans.

The term "anti-thrombotic composition" as used in the subject invention refers to a composition comprising a fibrin-specific monoclonal antibody, or fragment or derivative thereof, and a pharmaceutically acceptable carrier, that in sufficient amount can inhibit thrombus formation in a human in need of said inhibition.

The term "effective dose" as used in the subject invention is meant to refer to that amount of monoclonal antibody, or fragment or derivative thereof, that is large enough to inhibit thrombus formation in a human in need of such treatment. The dosage should not be so large as to cause adverse side effects, such as unwanted cross-reactions or anaphylactic reactions and the like. Generally, the dosage will vary with the age, condition, sex, and extent of disease in the patient, counter-indications, if any, immune tolerance, and other such variables, to be adjusted by the individual physician. Although dosages will vary depending upon individual sets of circumstances, in most cases of vascular disease and under most surgical conditions the dose will be determined by the body weight of the human in need of treatment, ranging from about 1 µg/kg body weight to about 50 µg/kg body weight, and preferably ranging from about 5 µg/kg body weight to about 10 µg/kg body weight.

Methods of Administration

Fibrin-specific monoclonal antibodies, or fragments or derivatives thereof, can be administered to a human by any appropriate mode, including parenterally by single bolus injection, continual infusion, or by a combination of these two methods. Administration can also be by direct infusion with a catheter, such as in intracoronary administration, where indicated.

Preparations for parenteral administration include, for example, reconstitution of lyophilized fibrin-specific monoclonal antibodies, or fragments or derivatives thereof, in sterile, endotoxin-free, physiological saline, or, more generally, may include reconstitution or dispersal of fibrin-specific monoclonal antibodies, or fragments or derivatives thereof, in sterile aqueous or non-aqueous solutions, suspensions, and emulsions. Examples of non-aqueous solvents are propylene glycol, polyethylene glycol, vegetable oil such as olive oil, and injectable organic esters such as ethyloleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. It is preferred that the pharmaceutical compositions of the subject invention be in sterile form so as to meet the sterility standards set forth by the United States Food and Drug Administration.

The subject invention further provides pharmaceutical kits comprising one or more of the ingredients of the pharmaceutical compositions of the invention stored in the same or separate containers. Optionally associated with such container(s) can be a notice in the form prescribed by a governmental agency regulating the manufacture, use or sale of pharmaceuticals or biological products, which notice reflects approval by the agency of manufacture, use or sale for human administration. Optionally associated with kits that contain only lyophilized antibody, or fragments or derivatives thereof, can be instructions as to which carriers are appropriate for administration to a human in need of treatment.

Extent, duration, timing, and method of treatment will vary with the age, weight, condition, and sex of the human in need of treatment, as well as with the type and extent of the disease for which treatment is required, to be adjusted by the administering physician according to each set of circumstances. Treatment may be administered either immediately before, during, or after any surgical procedure, or both before and during the procedure, or both during and after the procedure, or before, during and after the procedure, depending upon the particular set of circumstances of the case.

For example, in the case of a surgical procedure such as balloon angioplasty, it is often the case that the human patient already has present a large number of widely dispersed blood clots. In this situation, it generally will be advantageous to administer the anti-thrombotic composition immediately after the angioplasty procedure is performed, preferably utilizing the angioplasty catheter while it is still in place, so as to directly flush the injured portion of the blood vessel with the anti-thrombotic composition, thereby focusing the treatment to that one site. This prevents the loss of the antithrombotic composition that would result, for example, from binding of antibody to thrombi at non-involved sites.

In situations involving invasive surgical procedures in patients with no history of pathological thromboses, it will generally be preferable to administer the anti-thrombotic composition either immediately before or during the procedure since there is less risk that the anti-thrombotic composition will be lost by binding at non-involved sites.

Furthermore, in most situations involving invasive surgical procedures, the time during which there is an increased danger that clots will form tends to be immediately after the procedure is completed. As a result, only a limited number of treatments, or even one treatment of sufficient duration, can suffice to effectively inhibit thrombus formation, thereby substantially reducing the risk of surgery-induced clotting with its attendant risks to the patient.

In the case of chronic thrombotic disease, the timing, duration, and number of anti-thrombotic treatments depends greatly upon pre- and post-treatment diagnosis of the patient's condition and response to preliminary anti-thrombotic treatment, which must be determined, monitored, and evaluated by the administering physician.

Determining the Efficacy of Treatment

Efficacy of anti-thrombotic treatment with the MH-1 monoclonal antibody, or with a fragment or derivative thereof, can be determined by standard methods. Examples of such methods include but are not limited to: (1) angiographic monitoring by the imaging of arterial or venous dye flow, where the appearance of obstructed dye flow indicates a need for further treatment; (2) by use of scintigraphy utilizing a thrombus-specific antibody conjugated to a radiolabel, where thrombus size and location can be monitored for signs that further treatment is required; (3) by monitoring the occurrence and degree of clinical symptoms, where an increase in the number or severity of symptoms can indicate a need for further treatment; and (4) by measuring the levels of fibrinogen in a person's blood, since there is an inverse relationship between fibrinogen and fibrin levels, wherein a drop in fibrinogen level can indicate a possible corresponding increase in fibrin level and fibrin polymerization, indicating a need for further treatment.

Having now generally described the subject invention, the same will become more readily understood by reference to a specific example included herein for purposes of illustration only, and which is not intended to be limiting.

Example: In Vitro Inhibition of Clotting

A series of in vitro experiments were performed to determine the influence of MH-1 on clotting. Purified human fibrinogen (Kabi, Chromogenix Co, Ohio) was dissolved in 150 mM phosphate buffered saline, at physiological pH, at 1 mg/ml concentration, and approximately 100 µl 693 placed in each well of a microtiter dish (Costar). To each well was added approximately 50 µl bovine thrombin at a final concentration of 0.5 NIH units/ml to form a reaction mixture. To the reaction mixture, at time zero, was added approximately 50 µl of either: (1) the MH-1 monoclonal antibody, to give a final antibody concentration of 100 µg/ml.; (2) the 45J monoclonal antibody (the 45J monoclonal antibody, which crossreacts with fibrin and fibrinogen, is secreted by hybridoma cell line ATCC No. HB 9740, which was made by conventional techniques utilizing a conventional Balb/c mouse, wherein the mouse was immunized with fibrin) to give a final antibody concentration of 200 µg/ml; or (3) physiological saline. The reaction was allowed to proceed for 60 min at 37° C. Clotting was measured spectrophotometrically at 340 nm every 2 minutes. An increase in absorbance indicated that clotting was progressing. The end of the clotting process was observable as a plateau in the curve of absorbance versus time.

FIG. 1 indicates that treatment with MH-1 inhibited the rate of clotting, as evident from the lower initial slope of the absorbance/time curve for the reaction mixture treated with MH-1, as compared to either the 45J control reaction mixture or the saline control reaction mixture (Fibrinogen). In addition, MH-1 reduced the absolute amount of clotting that occurred, as measured by the lower level of the curve's plateau as compared to the control reactions. The control reaction mixture containing the 45J antibody (at twice the concentration of MH-1) did not display any inhibition of clotting compared to the saline control reaction. This data supports the proposition that the MH-1 monoclonal antibody is capable of inhibiting thrombus formation.

Figure 2:
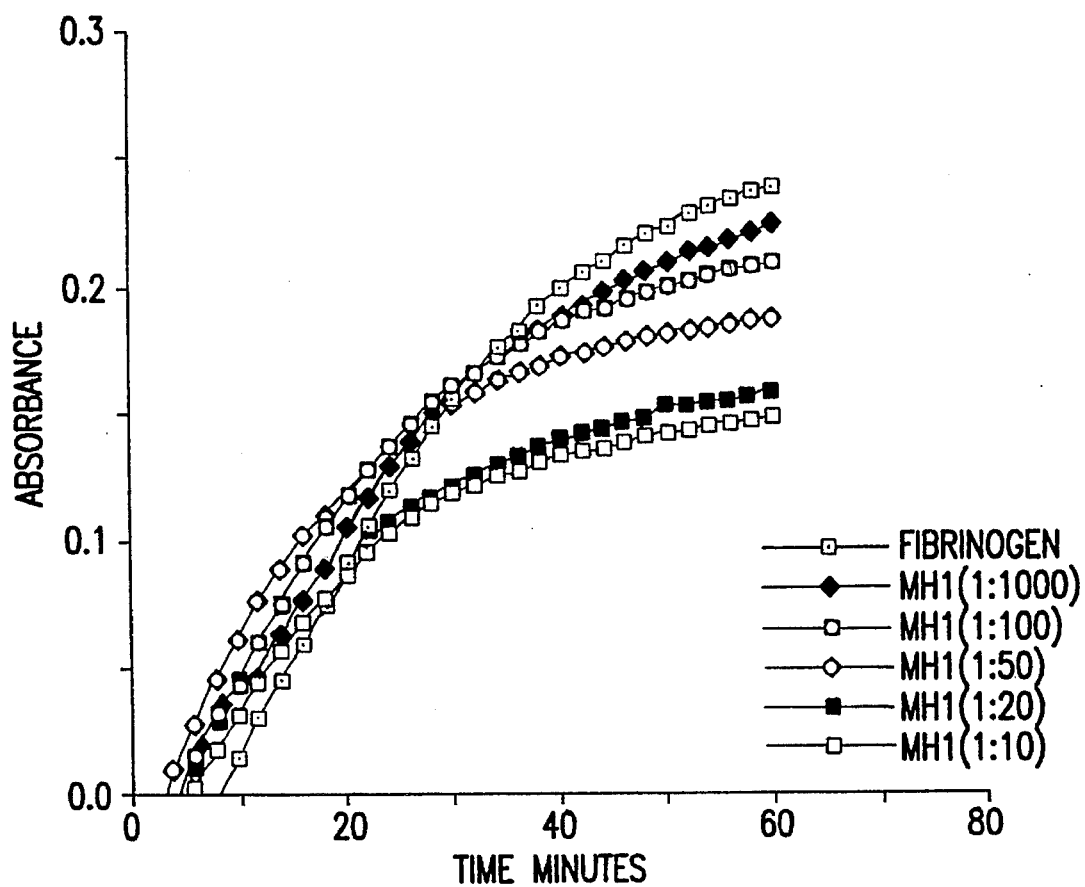
FIG. 2. Inclusion of an increasing amount of MH-1 monoclonal antibodies in a fibrinogen/thrombin clotting reaction mixture results in an increasing level of inhibition of clotting. "Fibrinogen" is a control reaction.

In a second experiment, the effect of several different concentrations of MH-1 on clotting time as compared to a fibrinogen control reaction was tested. FIG. 2 shows clotting reaction profiles (absorbance/time) indicating increasing inhibition of the clotting reaction with increasing concentration of MH-1 in the reaction mixture. (1:1000=1 µg/ml; 1:100=10 µg/ml; 1:50=20 µg/ml; 1:20=50 µg/ml; 1:10=100 µg/ml; Fibrinogen=control).

Deposit of Hybridoma

Hybridoma cell lines MH-1 and 45J were deposited with the American Type Culture Collection (ATCC) on Jun. 9, 1988 and given accession numbers HB 9739 and HB 9740, respectively. The ATCC is located at 12301 Parklawn Drive, Rockville, Md. 20852. MH-1 antibody is an $IgG_1$ antibody with a kappa light chain and it has been observed that the MH-1 antibody crossreacts with both human fibrin and rabbit fibrin.

The subject invention is not intended to be limited in scope to the deposited hybridoma cell line ATCC No. HB 9739 or to the MH-1 monoclonal antibody, but is intended as a single illustration of a fibrin-specific monoclonal antibody that inhibits thrombus formation. Any functionally equivalent fibrin-specific monoclonal antibody, or fragment or derivative thereof, is within the scope of the subject invention. By the term "functionally equivalent" it is meant that a monoclonal antibody, or fragment or derivative thereof, is capable of inhibiting thrombus formation by binding to the same epitope to which the MH-1 antibody binds.

The present invention may be embodied in other specific forms without departing from the spirit or essential attributes thereof, and, accordingly, reference should be made to the appended claims, rather than the foregoing specification, as indicating the scope of the invention.

All publications and patents cited above are herein incorporated by reference.

We claim:

1. A method for reducing the rate of fibrin deposition in a human, comprising administering to a human in need of said reduction an effective amount of the fibrin-specific monoclonal antibody MH-1 produced by hybridoma ATCC 9739, or an antibody that binds to the same epitope as monoclonal antibody MH-1.

2. The method of claim 1 comprising administering fibrin-specific monoclonal antibody MH-1.

3. A method for reducing the rate of fibrin deposition in a human, comprising administering to a human in need of said reduction an effective amount of a fragment or derivative of the fibrin-specific monoclonal antibody MH-1 produced by hybridoma ATCC 9739, or an antibody that binds to the same epitope as monoclonal antibody MH-1, which fragment or derivative contains the binding domain of said antibody.

4. The method of claim 3, comprising administering a fragment or derivative of the fibrin-specific monoclonal antibody MH-1.

5. A method for treating a human to reduce the human' risk of post-surgical thrombotic complications, comprising administering to a human in need of said treatment an effective amount of the fibrin-specific monoclonal antibody MH-1 produced by hybridoma ATCC 9739, or an antibody that binds to the same epitope as monoclonal antibody MH-1.

6. The method of claim 5, comprising and administering the fibrin-specific monoclonal antibody MH-1.

7. The method of claim 5, wherein said post-surgical thrombotic complications arise from angioplasty.

8. The method of claim 5, wherein said post-surgical thrombotic complications arise from organ transplantation.

9. A method for treating a human to reduce the human's risk of post-surgical thrombotic complications, comprising administering to a human in need of said treatment an effective amount of a fragment or derivative of the fibrin-specific monoclonal antibody MH-1 produced by hybridoma ATCC 9739, or an antibody that binds to the same epitope as monoclonal antibody MH-1, which fragment or derivative contains the binding domain of said antibody.

10. The method of claim 9, comprising administering a fragment or derivative of the fibrin-specific monoclonal antibody MH-1.

11. The method of claim 9, wherein said post-surgical thrombotic complications arise from angioplasty.

12. The method of claim 9, wherein said post-surgical thrombotic complications arise from organ transplantation.

13. A method for treating a thrombotic vascular disease in a human, comprising administering to a human in need of said treatment an effective amount of the fibrin-specific monoclonal antibody MH-1 produced by hybridoma ATCC 9739, or an antibody that binds to the same epitope as monoclonal antibody MH-1.

14. The method of claim 13, comprising administering the fibrin-specific monoclonal antibody MH-1.

15. The method of claim 13, in which the thrombotic vascular disease is stroke.

16. The method of claim 13, in which the thrombotic vascular disease is pulmonary embolism.

17. The method of claim 13, in which the thrombotic vascular disease is deep vein thrombosis.

18. The method of claim 13, in which the thrombotic vascular disease is arterial or venous thrombosis.

19. The method of claim 13, in which the thrombotic vascular disease is atherosclerosis.

20. A method for treating thrombotic vascular disease in a human, comprising administering to a human in need of said treatment an effective amount of a fragment or derivative of the fibrin-specific monoclonal antibody MH-1 produced by hybridoma ATCC 9739, or an antibody that binds to the same epitope as monoclonal antibody MH-1, which fragment or derivative contains the binding domain of said antibody.

21. The method of claim 20, comprising administering a fragment or derivative of the fibrin-specific monoclonal antibody MH-1.

22. The method of claim 20, in which the thrombotic vascular disease is stroke.

23. The method of claim 20, in which the thrombotic vascular disease is pulmonary embolism.

24. The method of claim 20, in which the thrombotic vascular disease is deep vein thrombosis.

25. The method of claim 20, in which the thrombotic vascular disease is arterial or venous thrombosis.

26. The method of claim 20, in which the thrombotic vascular disease is atherosclerosis.

* * * * *